United States Patent
Lehman

(10) Patent No.: US 10,716,747 B2
(45) Date of Patent: *Jul. 21, 2020

(54) SERUM FOR REDUCING THE TIME NEEDED TO DRY WET HAIR

(71) Applicant: HENKEL IP & HOLDING GMBH, Duesseldorf (DE)

(72) Inventor: Thomas A. Lehman, Indianapolis, IN (US)

(73) Assignee: HENKEL IP & HOLDING GMBH, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/069,679

(22) Filed: Nov. 1, 2013

(65) Prior Publication Data

US 2014/0140947 A1    May 22, 2014

Related U.S. Application Data

(60) Provisional application No. 61/721,245, filed on Nov. 1, 2012.

(51) Int. Cl.

| *A61K 8/39* | (2006.01) |
|---|---|
| *A61K 8/58* | (2006.01) |
| *A61K 8/81* | (2006.01) |
| *A61K 8/37* | (2006.01) |
| *A61Q 5/00* | (2006.01) |
| *A61Q 5/12* | (2006.01) |
| *A61K 8/891* | (2006.01) |
| *A61K 8/895* | (2006.01) |

(52) U.S. Cl.
CPC ............. *A61K 8/891* (2013.01); *A61K 8/39* (2013.01); *A61K 8/585* (2013.01); *A61K 8/8164* (2013.01); *A61K 8/895* (2013.01); *A61Q 5/12* (2013.01); *A61K 2800/31* (2013.01); *A61K 2800/54* (2013.01)

(58) Field of Classification Search
None
See application file for complete search history.

(56) References Cited

U.S. PATENT DOCUMENTS

| 2002/0102225 A1 | 8/2002 | Hess et al. | |
|---|---|---|---|
| 2005/0220828 A1* | 10/2005 | Ullom | A45D 44/00 424/401 |
| 2007/0243143 A1 | 10/2007 | Patil et al. | |
| 2007/0248550 A1 | 10/2007 | Patel et al. | |
| 2007/0269389 A1 | 11/2007 | Fuscelli et al. | |
| 2009/0165812 A1 | 7/2009 | Resnick et al. | |
| 2010/0012142 A1 | 1/2010 | Presti | |
| 2010/0028272 A1 | 2/2010 | Knappe et al. | |
| 2010/0092408 A1 | 4/2010 | Breyfogle et al. | |
| 2011/0077083 A1 | 3/2011 | Ahn et al. | |
| 2011/0268684 A1* | 11/2011 | Battermann et al. | 424/70.11 |
| 2012/0064482 A1 | 3/2012 | Boehm et al. | |
| 2012/0076842 A1 | 3/2012 | Fournial et al. | |
| 2012/0276035 A1 | 11/2012 | Lehman, Jr. | |

OTHER PUBLICATIONS

Schaefer (Silicones in Hair Care: Making Innovative Solutions Possible)(2007) Retrieved from: http://www.cosmeticsandtoiletries.com/formulating/function/moisturizer/7653302.html#sthash.vtVJlisw.dpuf.*
International Search Report and Written Opinion, dated Feb. 24, 2014, PCT/US2013/067993, pp. 1-12.
Final Office Action from U.S. Appl. No. 13/097,773, dated Oct. 11, 2013, pp. 1-16.
European Search report regarding related application EP 13 85 0439 dated Apr. 15, 2016, 5 pages.
Database GNPD (online), "Anti-Frizz Spray" XP-002755890, Apr. 2, 2012, 3 pages.
Database GNPD (online), "Conditioner" XP-002755891, Nov. 1, 2010, 3 pages.
Database GNPD (online), "Glaze Haze Semi-Sweet Smoothing Hair Serum" XP-002755892, Nov. 1, 2011, 3 pages.

* cited by examiner

*Primary Examiner* — Patricia Duffy
*Assistant Examiner* — Garen Gotfredson
(74) *Attorney, Agent, or Firm* — Lorenz & Kopf LLP

(57) ABSTRACT

A non-aqueous composition and method for reducing the drying time of wet hair includes applying added water to human hair to obtain wet hair and applying a nonaqueous serum comprising a combination of about 55 to about 65 percent by weight of at least one volatile silicone compound, about 30 to about 40 percent by weight of at least one high molecular weight silicone elastomer, a thermoprotective agent, an emollient, and a conditioning agent; applying the nonaqueous serum and heat to the wet hair in order to remove from about 80% to about 100% of the added water. In one embodiment, the application of the serum is capable of reducing a drying time of the wet hair by at least 25 percent.

5 Claims, 1 Drawing Sheet

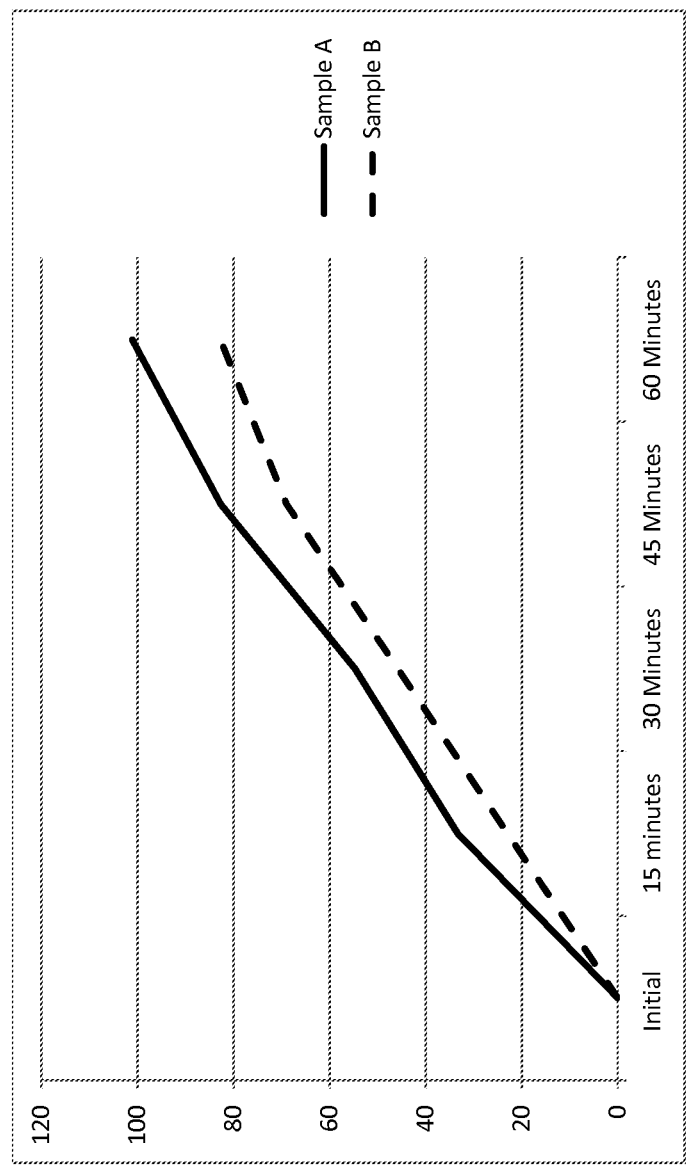

SERUM FOR REDUCING THE TIME NEEDED TO DRY WET HAIR

RELATED APPLICATIONS

This application claims priority to U.S. Provisional Patent Application No. 61/721,245 filed on Nov. 1, 2012, entitled Serum for Reducing the Time Needed to Dry Wet Hair.

FIELD OF THE INVENTION

The present disclosure relates to serums for use in hair that are capable of reducing the time needed to blow dry wet hair. In addition, the serums may include those that thermally protect, reduce frizz, and/or soften hair and leave-in treatments that can be applied to hair as a mist.

BACKGROUND

In order to create hairstyles, treatment compositions in the form of setting lotions, aerosol and non-aerosol sprays, setting foams, and gels are used. It would be desirable to provide users with a composition that also decreased drying time for hair, especially for those users with long or thick hair. Many attempts have been made to reduce the drying time of hair, but the known compositions form coatings on hair, making it less water repellent and therefore less efficient in decreasing time to dry hair; also the coatings are less resistant towards washing with shampoo and gets degraded more rapidly. It would be desirable to develop a formulation that could be applied after the hair is washed and would also not leave a residue on the clean hair.

SUMMARY

A nonaqueous serum for reducing the drying time of wet hair has a density of about 1.02 g/ml and includes a nonaqueous combination of at least one volatile silicone compound and at least one silicone elastomer. In one embodiment, the volatile silicone compound includes from about 55 percent to about 65 percent or about 60 percent to about 63 percent cyclopentasiloxane and the at least one silicone elastomer comprises about 30 to about 40 percent or about 34 percent to about 38 percent by weight of a dimethicone crosspolymer in dimethicone.

The serum may also include at least one cosmetically acceptable additive, such as a thermoprotective agent. In one embodiment, the thermoprotective agent includes sodium laneth-40 maleate/styrene sulfonate copolymer. The serum may also include a second cosmetically acceptable additive, such as a fragrance, an essential oil, a conditioning agent, or an emollient.

DESCRIPTION OF THE DRAWINGS

FIG. 1 is a graphical representation of the percent of water lost in Samples A and B as a function of time.

DETAILED DESCRIPTION

The serum includes a combination of silicone compounds. The serum can be applied with as a thick fluid or gel or in other suitable forms. The serum may include small amounts of water, less than about one percent, but is nonaqueous. For the purposes of this disclosure, serums that include less than about one percent water are considered to be nonaqueous. The serum includes at least one volatile silicone compound and at least one, but preferably a combination of at least two, silicone elastomers. The serum may also optionally include emollients, thermal protective agents, conditioning agents, and perfumes. The serum may preferably have a density of about 1.02 g/ml. The serum may also be preferably colorless.

The serum includes at least one volatile silicone compound, such as cyclopentasiloxane (D5), cyclomethicone (D4), and/or a substituted or an unsubstituted methyl silsesquioxanes. Suitable volatile silicone compounds include XIAMETER® PMX-0245 CYCLOPENTASILOXANE (formerly DC 245) from Dow Corning. Other suitable cyclopentasiloxanes may be available from Wacker, ISP, Rhodia, Jeen Corp., and Momentive Performance Materials. As used herein, the term "volatile" when employed in relation to a silicone compound includes compounds that exhibit a vapor pressure of more than about 0.2 mm Hg at 25° C. at one atmosphere of pressure or have a boiling point at one atmosphere of less than the boiling point of water, i.e. less than about 100° C.

Examples of suitable cyclomethicones may include Dow Corning 200 Fluid, Dow Corning 244 Fluid, Dow Corning 344 Fluid, and Dow Corning 345 Fluid (each commercially available from Dow Corning Corp.); SF-1204 and SF-1202 Silicone Fluids (each commercially available from G. E. Silicones), GE 7207 and 7158 (each commercially available from General Electric Co.); and SWS-03314 (each commercially available from SWS Silicones Corp.).

Examples of suitable methyl silsesquioxanes may include TMF 1.5 fluid (commercially available from Shin-Etsu Chemical Co), phenyl substituted silsesquioxanes (commercially available from Clariant as Silcare 15M60), n-Octyl substituted silsesquioxanes (commercially available as Silcare 31M60 and 31M50), hexyl methicone, caprylyl methicone, and lauryl methicone (each commercially available from Clariant as Silcare 41M10, 41M15 and 41M20, respectively).

The serum includes from about 50 to about 75 percent by weight of one or more volatile silicone compounds, from about 60 to about 70 percent by weight of one or more volatile silicone compounds, or from about 60 to about 65 percent by weight of one or more volatile silicone compounds. All weight percentages disclosed herein are based upon the weight of the final serum, unless otherwise stated. In certain embodiments, the volatile silicone compound may be cyclopentasiloxane.

The serum also includes at least one silicone elastomer. Broadly, uncoated forms of cosmetically acceptable silicone elastomers may be used in the serum. These elastomers are considered non-emulsifying because they do not contain any appreciable amount of polyoxyalkylenes. Uncoated silicone elastomers include cross-linked or partially cross-linked cyclomethicone (and) dimethicone crosspolymers. Commercially available examples of suitable silicone elastomers include DC-9040, DC-9041 and DC-9045 (available from Dow Corning Inc), KSG-15 and USG-103 (available from Shin-Etsu Silicones of America), and GE 1229 (available from General Electric Silicones, Waterford, N.Y.).

In one embodiment, the serum includes a combination of silicone elastomers. Specifically, the serum may include from about 20 to about 45 percent by weight of a mixture of dimethicone and a dimethicone crosspolymer, and preferably from about 35 to about 40 percent of the mixture. One specific example of a suitable silicone elastomer is DC 9041, commercially available from Dow Corning.

The serum may also optionally include other cosmetically acceptable additives, such as emollients, thermal protective agents (a.k.a. thermoprotective agent), hair conditioning agents, fragrance, and essential oils. Suitable oils may include, but are not limited to, agar, argan, balsam, basil, bay, bergamot, cardamom seed, cedarwood, cranberry, frankincense, geranium, grapefruit, jasmine, jojoba seed, lavender, lemon, litsea cubeba, orange, orris, parsley, patchouli, rose, rosemary, rosewood, sassafras, savory oil, star anise, tangerine oils, and combinations thereof.

In one embodiment, the serum may optionally include one or more of (1) from about 0.01 to about 1.0 percent by weight, preferably about 0.1 to about 0.3 percent by weight, argan oil, (2) from about 0.01 to about 1.0 percent by weight, preferably about 0.1 to about 0.3 percent by weight, jojoba seed oil, and (3) from about 0.1 to about 2.0 percent by weight, preferably 0.2 to about 0.5 percent by weight, of a fragrance additive.

In one embodiment, the serum may include at least one emollient, such as ppg-3 benzyl ether myristate, or other suitable thermal protector. One commercially available emollient is Crodamol STS from Croda.

In one embodiment, the serum may include at least one thermal protective agent, such as a sodium laneth 40 maleate/styrene sulfonate copolymer, or other suitable thermal protector. One commercially available thermal protective agent is Mirustyle X-HP from Croda. Another example is commercially available as Mirustyle X-HV from Croda.

EXAMPLE

The serum is illustrated by the following non-limiting example. The serum is prepared by mixing the following ingredients according to the amounts in Table I below:

TABLE I

| Component | Weight % |
|---|---|
| Cyclopentasiloxane[1] | 61.30 |
| High Molecular Weight Silicone Elastomer in Dimethicone[2] | 37.00 |
| PPG-3 Benzyl Ether Myristate[3] | 1.00 |
| Sodium Laneth 40 Maleate/Styrene Sulfonate Copolymer[4] | 0.001 |
| Mango Melody[5] | 0.50 |
| Argan Oil[6] | 0.10 |
| Jojoba Seed Oil[7] | 0.10 |

[1]Available from Dow Corning under the trade name DC 245
[2]Available from Dow Corning under the trade name DC 9041 and described by Dow Corning as a dimethicone (and) dimethicone crosspolymer
[3]Available from Croda under the trade name Crodamol STS
[4]Available from Croda under the trade name Mirustyle XHP
[5]Available from Belmay Fragrances
[6]Available from Charkit Chemical Corporation
[7]Available from Columbus Foods In the example provided in Table I, batches, in either 1 or 2 pound quantities, of the blow dry treatment were prepared by individually adding 61.30% by weight cyclopentasiloxane (DC 245) to a Caframo lab mixer having three blades with a total diameter of 2-2.5 inches. At a moderate mixing speed 37.00% by weight of the silicone elastomer in dimethicone was added. The ingredients were then blended. When the cyclopentasiloxane and silicone elastomer are fully blended, the remaining ingredients were added one by one to form the treatment serum. In other embodiments, it is contemplated that one, all, or none of fragrance and oils may be included in the final treatment serum. It is also noted that the overall final treatment serum may include as much as, but no more than 1.0% water, by weight.

The final treatment serum prepared according to Table I was found to be capable of reducing the drying time of wet hair. For purposes of this disclosure, to "dry" wet hair means to remove at least 85% of added water weight. To be capable of reducing the drying time of wet hair, the serum decreases the time, in minutes, needed to evaporate from 85% to 100% of the added water weight on a swatch of human hair when subjected to a pre-selected amount of heat, as compared to a similar, but untreated, swatch of hair subjected to the same amount of heat.

In order to compare the time needed to blow dry wet hair, the dry weight of hair swatches was measured. Each swatch, Samples A and B, was submerged in water and uniformly towel blotted to remove some amount of water. The towel-dried wet swatches were then weighed. About 0.45 to about 0.5 g total of the serum made according to the specifications of Table I was applied to Sample A.

The samples were placed under a conventional hood drier set on perm, 120° F. (±2° F.), and allowed to dry for 15 minutes. All samples were then weighed. This procedure was repeated an additional three times, for a total of 60 minutes of time under the drier hood for all of the samples.

The weight percent of water loss for the treated sample A and untreated sample B was calculated by comparing the weight of water removed at various time intervals. The weight percent of added water lost over the course of an hour is set forth in Table II below and FIG. 1.

TABLE II

| | % Added Water Removed | | | | |
|---|---|---|---|---|---|
| | Initial | 15 Min | 30 min | 45 min | 60 min |
| A | 0.0 | 33.33 | 54.72 | 82.68 | 101.13 |
| B | 0.0 | 22.98 | 45.77 | 68.95 | 82.73 |

As demonstrated above, embodiments prepared according to the present disclosure decrease the time needed to dry wet hair by up to 50%.

In use, the serum may be applied to wet hair, i.e. hair that has had water added to it, for example, during washing. After the hair is towel dried, the serum may be worked throughout the damp hair. Once applied, heat is then added to the hair by a blow drier or other suitable methods. In one embodiment, the time needed to dry a user's hair is decreased by about 20 to about 30%, however the time needed to dry the user's wet hair may be decreased by as much as 50%. The serum may also be applied to dry hair to control fizz and add shine.

While the composition and methods herein have been described with a number of embodiments, the scope is not intended to be limited by the specific embodiments. Modifications and variations from the described embodiments exist. Although numerous ingredients suitable for formulating the hair styling composition have been listed, the list is by no means exhaustive. It is, of course, not possible to describe every conceivable combination of components or methodologies for purposes of describing the systems, methods, devices, and so on, described herein. Additional advantages and modifications will readily appear to those skilled in the art. Therefore, the invention is not limited to the specific details, the representative revascularization catheter systems, and illustrative examples shown and described. Thus, this application is intended to embrace alterations, modifications, and variations that fall within the scope of the appended claims. Furthermore, the preceding description is not meant to limit the scope of the invention. Rather, the scope of the invention is to be determined by the appended claims and their equivalents.

The invention claimed is:

1. A nonaqueous serum capable of reducing the drying time of wet hair, consisting of:
   61.3 percent by weight of cyclopentasiloxane;
   37.0 percent by weight of a silicone elastomer in dimethicone, wherein the silicone elastomer is a dimethicone crosspolymer;
   1.0 percent by weight of ppg-3 benzyl ether myristate;
   0.001 percent by weight of a thermoprotective agent consisting of a sodium laneth 40-maleate/styrene sulfonate copolymer, and
   0.07 percent by weight of additives,
   wherein the serum has a density of about 1.02 g/ml and is applied to a wet hair and the application of the serum removes more than about 80% of added water weight from the wet hair upon exposure to a pre-selected amount of heat.

2. The nonaqueous serum of claim 1, wherein the additives are selected from one or more of fragrance, argan oil, and jojoba oil.

3. A method for reducing the drying time of wet hair, composing:
   applying added water to human hair to obtain wet hair;
   supplying the nonaqueous serum of claim 1;
   applying the nonaqueous serum to the wet hair;
   applying heat to the wet hair; and
   removing from about 80% to about 100% of the added water;
   wherein the application of the serum is capable of reducing a drying time of the wet hair by at least 25 percent.

4. A nonaqueous serum for reducing the drying time of wet hair, consisting of:
   a nonaqueous combination of 60 to 63 percent by weight of cyclopentasiloxane, 34 to 38 percent by weight of a silicone elastomer in dimethicone, wherein the silicone elastomer is a dimethicone crosspolymer, 0.001 percent by weight of a thermoprotective agent consisting of a sodium laneth 40-maleate/styrene sulfonate copolymer, and 0.1 to 0.3 percent by weight of cosmetically acceptable additive comprising jojoba seed oil,
   wherein the serum is characterized by having less than 1% water and has a density of about 1.02 g/ml, and wherein the serum when applied on damp hair removes at least 80% of added water weight from the damp hair upon exposure to a pre-selected amount of heat.

5. The serum of claim 4, wherein the cosmetically acceptable additive is selected from the group consisting of an emollient, a hair conditioning agent, a fragrance, and an oil.

* * * * *